United States Patent
Brown et al.

(10) Patent No.: US 10,149,986 B2
(45) Date of Patent: *Dec. 11, 2018

(54) OPTOGENETIC CONTROL OF ENDOTHELIAL CELLS

(71) Applicants: Brown University, Providence, RI (US); Massachusetts Institute of Technology, Cambridge, MA (US)

(72) Inventors: Tyler C. Brown, Quincy, MA (US); Christopher I. Moore, Pawtucket, RI (US)

(73) Assignees: Brown University, Providence, RI (US); Massachusetts Institute of Technology, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/633,143

(22) Filed: Jun. 26, 2017

(65) Prior Publication Data

US 2018/0015296 A1 Jan. 18, 2018

Related U.S. Application Data

(63) Continuation of application No. 14/421,744, filed as application No. PCT/US2013/054675 on Aug. 13, 2013, now Pat. No. 9,687,672.

(60) Provisional application No. 61/682,514, filed on Aug. 13, 2012.

(51) Int. Cl.
| | |
|---|---|
| *A61N 5/06* | (2006.01) |
| *A61K 41/00* | (2006.01) |
| *A01K 67/027* | (2006.01) |
| *C07K 14/47* | (2006.01) |
| *C12M 1/42* | (2006.01) |
| *A61K 48/00* | (2006.01) |
| *A61N 5/067* | (2006.01) |

(52) U.S. Cl.
CPC .......... *A61N 5/062* (2013.01); *A01K 67/0275* (2013.01); *A61K 41/0057* (2013.01); *A61N 5/0601* (2013.01); *A61N 5/0618* (2013.01); *C07K 14/4702* (2013.01); *C12M 35/02* (2013.01); *A01K 2217/052* (2013.01); *A01K 2217/206* (2013.01); *A01K 2227/105* (2013.01); *A01K 2267/0393* (2013.01); *A61K 48/005* (2013.01); *A61N 2005/0602* (2013.01); *A61N 2005/063* (2013.01); *A61N 2005/067* (2013.01); *A61N 2005/0652* (2013.01); *A61N 2005/0663* (2013.01); *C07K 2319/60* (2013.01); *C12N 2799/021* (2013.01)

(58) Field of Classification Search
None
See application file for complete search history.

(56) References Cited

U.S. PATENT DOCUMENTS

| | | | |
|---|---|---|---|
| 9,687,672 | B2 | 6/2017 | Brown et al. |
| 2007/0141163 | A1 | 6/2007 | Vitaliano et al. |
| 2009/0088680 | A1 | 4/2009 | Aravanis et al. |
| 2011/0301529 | A1 | 12/2011 | Zhang et al. |
| 2013/0137113 | A1 | 5/2013 | Isacoff et al. |

FOREIGN PATENT DOCUMENTS

| | | |
|---|---|---|
| WO | WO-2009/019508 A1 | 2/2009 |
| WO | WO-2011/005978 A2 | 1/2011 |
| WO | WO-2012/054484 A1 | 4/2012 |

OTHER PUBLICATIONS

Emerich et al., "Central analgesic actions of loperamide following transient permeation of the blood brain barrier with Cereport (RMP-7)," 801(1-2):259-66 (1998).
International Preliminary Report on Patentability for International Patent Application No. PCT/US2013/54675, dated Feb. 26, 2015 (9 pages).
International Search Report and Written Opinion for International Application No. PCT/US2013/54675, dated Dec. 16, 2013 (27 pages).
Reinbothe et al., "Optogenetic control of insulin secretion in intact pancreatic islets with beta-cell-specific expression of Channelrhodopsin-2," Islets. 6(1):e28095 (2014) (8 pages).

*Primary Examiner* — Nancy J Leith
(74) *Attorney, Agent, or Firm* — Clark & Elbing LLP

(57) ABSTRACT

The invention features methods for regulating vascular properties by controlling the membrane properties of endothelial cells using optogenetics and light. The invention features methods to transport therapeutics across the vascular barrier into tissues such as the brain and the lung, with high spatial and temporal precision, and for controlling vascular properties such as vascular tone, arterial diameter, and vascular growth.

14 Claims, 4 Drawing Sheets

OPTOGENETIC CONTROL OF ENDOTHELIAL CELLS

STATEMENT AS TO FEDERALLY FUNDED RESEARCH

This invention was made with government support under Grant No. F32 NS078895, awarded by the National Institutes of Health. The government has certain rights in this invention.

BACKGROUND OF THE INVENTION

The invention features methods for regulating vascular properties by controlling endothelial cell behavior using optogenetic reagents and light, and uses thereof. In certain embodiments, the invention features methods for regulating the permeability of the blood-brain barrier for delivery of therapeutics to the brain and for regulating vascular tone and vascular growth.

Drugs injected via intravascular (IV) injections provide an optimal pathway for the non-invasive delivery of therapeutics to the brain. The primary impediment to optimal IV use is the blood-brain barrier (BBB). This barrier is crucial for normal brain function, preventing cross-talk between blood elements and the brain. In medical practice, the BBB is an obstacle and prevents almost all beneficial drugs from entering the brain.

Given the importance of BBB opening for drug delivery, several approaches have been attempted to open or circumvent the BBB. Agents such as mannitol, which creates a hyper-osmotic condition, or adenosine, are non-specific in space—they open the entire BBB—and at best have minimal open duration of tens of minutes and often compromise the BBB for hours. A second 'global' approach has been drug synthesis to mimic elements that naturally pass the BBB. These 'trojan horses' emulate small molecules to use their BBB ferrying systems, or engage large molecule receptor mediated transfer. This approach has significant promise, but suffers from the basic challenge of spatial and temporal precision endemic to any existing IV method, and it requires molecular engineering for each agent (alterations that could impact drug efficacy).

Currently, a single established method claims to provide non-invasive spatio-temporal precision in BBB opening—localized ultrasound pulsing of micro-bubbles injected IV. The mechanisms underlying this breach of the BBB are not known, but are believed to occur through mechanical aggravation of the endothelial cell (EC) layer that is the primary constituent of the BBB. This method is undesirable for several reasons. First, each opening of the BBB is technically complex—magnetic resonance imaging (MRI) is required to guide focusing of ultrasound to obtain spatial specificity. Second, the 'transient' opening achieved by this technique compromises the BBB for at least 3-5 hours. Third, the method works through an aphysiological mechanical BBB rupture, which is unlikely to allow multiple uses without creating chronic local reactivity or damage.

Thus there is a need for non-invasive and simple methods for the regulation of vascular permeability, especially in the BBB, with high spatial and temporal precision for delivery of therapeutics.

Several maladies result from failures in proper vascular tone, arterial diameter or improper vascular growth (angiogenesis). Thus there is also a need for non-invasive methods for controlling vascular tone, arterial diameter and vascular growth.

SUMMARY OF THE INVENTION

The invention features a method for changing the permeability of endothelial cells. The method generally includes the steps of contacting endothelial cells expressing optogenetic reagents with light and activating the optogenetic reagents with light, thereby changing the permeability of the endothelial cells.

In one embodiment, the invention features a method for changing the permeability of endothelial cells by a) infecting endothelial cells with recombinant viruses comprising a recombinant nucleic acid encoding an optogenetic reagent to produce infected endothelial cells; and b) contacting the infected endothelial cells with light, wherein the light activates the optogenetic reagents and thereby changes the permeability of the endothelial cells.

In another embodiment, the invention features a method to deliver a therapeutic across the blood-brain barrier by a) infecting endothelial cells with recombinant viruses comprising a recombinant nucleic acid encoding the optogenetic reagent to produce infected endothelial cells; b) introducing the therapeutic (e.g., drugs, small molecules, peptides, proteins, antibodies, nucleic acid molecules, and organic and inorganic compounds) into the blood stream; and c) contacting the infected endothelial cells with light, to activate the optogenetic reagents and thereby change the permeability of the endothelial cells and open the blood-brain barrier such that the therapeutic in the blood stream crosses the blood-brain barrier.

The invention also features methods to change the permeability of endothelial cells, which are part of a blood-brain barrier, such that this change in permeability results in opening or closing of the BBB. Such opening and closing of the BBB results in increased or decreased delivery of elements (e.g., therapeutic agents) from the endothelial cells to the brain.

The methods of the invention can be used, e.g., to regulate vascular tone, regulate arterial diameter, control blood flow to a region of a tissue, control delivery of blood-borne factors, and regulate vascular growth in a subject.

The methods of the invention can be used, e.g., to treat, or treat prophylactically a brain disease (e.g., glioma, epilepsy, Alzheimer's disease, multiple sclerosis, and meningitis). The method of the invention can also be used to treat or treat prophylactically a vascular disease caused by failure in proper vascular tone (e.g., stroke, aneurysm, diabetes, hypertension, and cardiac disease). Alternatively, the methods of the invention can be used to treat or treat prophylactically a disease caused by abnormal vascular growth (e.g., retinopathy, cerebrovascular epilepsy, and cancer).

Another aspect of the invention features methods to change the permeability of endothelial cells that are part of the blood-air barrier in the lung. These methods can be used to treat a disease of the lung (e.g., lung cancer).

In the methods of the invention, the optogenetic reagents can be, for example, ChR1, ChR2, VChR1, ChR2 C128A, ChR2 C128S, ChR2 C128T, ChD, ChEF, ChF, ChIEF, NpHR, eNpHR, Arch 3.0, Arch T 3.0, Mac 3.0, melanopsin, chimeras of these proteins, or natural or engineered variants thereof.

In another aspect of the invention, the optogenetic reagents are expressed in the endothelial cells by introducing a recombinant nucleic acid encoding the optogenetic reagent into the cells or precursors thereof. The recombinant nucleic acid can be introduced into the cells by using any suitable approach, e.g., virus, an electroporation device, transfection, or by way of a transgenic method.

If desired, the recombinant nucleic acid can be encapsidated within a recombinant virus selected from the group consisting of recombinant adeno-associated virus (AAV), recombinant retrovirus, recombinant lentivirus, recombinant poxvirus, recombinant rabies virus, recombinant pseudorabies virus, and recombinant herpes simplex virus, and human immunodeficiency virus (HIV).

The recombinant nucleic acid encoding the optogenetic reagents can also encode a fiducial (e.g., a fluorescent protein such as green fluorescent protein) marker, that when expressed identifies the cells that have been infected by the recombinant virus indicating that these cells will express the optogenetic reagent.

Any route of administration can be used to deliver the virus. For example, the virus may be applied using intravenous injection or applied locally to infect endothelial cells in specific regions.

In addition, light may be applied using a laser or a light emitting diode, and the application of light maybe restricted to a defined spatial region of the body. The light can be delivered using a fiber optic cable or catheter. The methods of the invention also involve light being shined on a specific region of the brain for a specific period of time, thus providing spatial and temporal control of the opening of the BBB.

Definitions

The term "optogenetic control" refers to the control of physiological properties of a cell by introducing a light-activated molecular channel (e.g., channnelrhodopsin-2) into the membrane of cells by genetic means; and contacting these cells with light of a wavelength that activates the molecular channel and causes a change in the membrane properties of the cell.

By "endothelial cells" is meant cells that line the interior surface of blood vessels.

By "expressing optogenetic reagents" is meant the production of one or more exogenous light-activated agents that impact cell physiology, most notably molecular channel proteins, in a cell into which a recombinant nucleic acid molecule encoding the light-activated molecular channel protein has been introduced by genetic means.

By "optogenetic reagents" is meant natural or engineered variants of light-activated agents that impact cell physiology, most notably molecular channel proteins, including elements such as channelrhodopsin, halorhodopsin, melanopsin and archaerhodopsin (e.g., ChR1, ChR2, VChR1, ChR2 C128A, ChR2 C128S, ChR2 C128T, ChD, ChEF, ChF, ChIEF, NpHR, eNpHR, Arch 3.0, Arch T 3.0, Mac 3.0). Exemplary optogenetic reagents are provided in Table 1.

By "electroporation" is meant a method of introducing exogenous nucleic acid molecules into cells by applying an external electric field that causes an increase in the permeability of the cell plasma membrane and uptake of the nucleic acid molecules into the cell.

By "transfection method" is meant a method of introducing exogenous nucleic acid molecules into mammalian cells by chemically opening pores in the cell membrane (e.g., by application of calcium phosphate), to allow uptake of the exogenous nucleic acid molecules. Alternatively, transfection may also be performed by mixing a cationic lipid with the exogenous nucleic acid molecules to produce liposomes that fuse with the cell membrane and deposit the exogenous nucleic acid molecules inside cells.

By "transgenic method" is meant a method of introduction of recombinant nucleic acid molecules into the genome of the organism.

By "fiducial marker" is meant a genetically encoded protein (e.g., a fluorescent protein) that enables identification of cells expressing the recombinant light-activated molecular channel.

By "defined spatial region" is meant a predetermined, specific, and confined area of the body.

By "blood-brain barrier" is meant the membrane structures and cell-to-cell contacts that protect the brain from chemicals in the blood, while still allowing essential metabolic function. The blood-brain barrier is composed of endothelial cells, which are packed very tightly in brain capillaries. The blood-brain barrier includes the blood-retinal barrier.

By "opening of the blood-brain barrier" is meant an increase in the permeability of endothelial cells in the blood-brain barrier, such that there is an increase in the transport of elements from the blood vessel, across the blood-brain barrier, into the brain.

By "closing of the blood-brain barrier" is meant a decrease in the permeability of endothelial cells in the blood-brain barrier, such that there is a decrease in the transport of elements from the blood vessel, across the blood-brain barrier, into the brain.

By "vascular tone" is meant the state of contractile tension in blood vessel walls.

By "arterial diameter" is meant the diameter of arteries.

By "vascular growth" is meant the creation of new blood vessels.

By "vasodilation" is meant the increase in the vascular diameter. Terms "vasodilation" and "vascular dilation" are used herein interchangeably.

By "vasoconstriction" is meant the decrease in the vascular diameter. Terms "vasoconstriction" and "vascular constriction" are used herein interchangeably.

By "luciferase" is meant an enzyme that is capable of converting chemical energy into light.

By "luciferin" is meant a compound that upon reaction in the presence of a luciferase emits light.

DETAILED DESCRIPTION OF THE INVENTION

Figure 1:
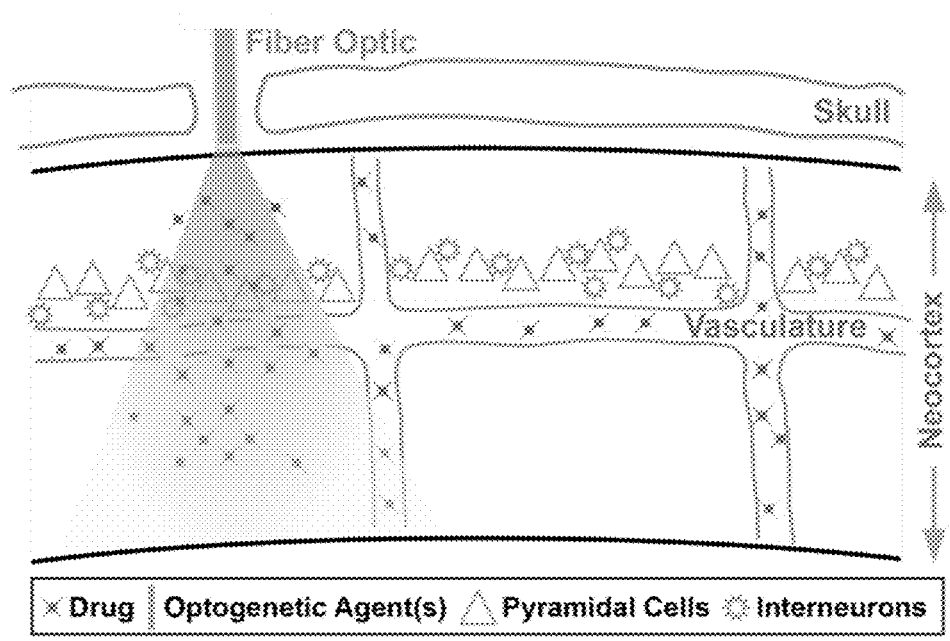
FIG. 1 is a schematic describing the BBB Integrated Optogenetics (BBBIO) method for precise control of endothelial cell (EC) function. Optogenetic reagents are expressed system-wide in vascular ECs. Local presentation of light of a first color, allows opening of the BBB at a precise location in the brain. Presentation of a second color of light, driving a different optogenetic reaction, can then be used to close the BBB, providing precise temporal control of BBB permeability.

The invention features methods for regulating vascular permeability by controlling endothelial cell behavior using optogenetic reagents and light. One aspect of the invention (named BBBIO) features optogenetic methods for precise spatial and temporal control of opening and closing of the BBB in order to deliver IV-injected therapeutics to the brain by regulating the permeability of endothelial cells, the primary constituent of the BBB. The invention can also be used for regulating vascular properties in other areas of the body such as the blood-lung barrier, also lined by endothelial cells. The method can also be used for regulating vascular properties such as vascular tone, arterial diameter, and vascular growth (angiogenesis). As an example, the use of the methods of the invention in regulating the BBB is described below.

The Blood-Brain Barrier (BBB): A Major Obstacle in Vascular Delivery of Therapeutics for Treatment of Brain Diseases The vasculature provides many advantages as a non-invasive pathway for delivering drugs to the brain. Intravascular (IV) injections reach their targets rapidly: vascular delivery initiated in the ascending system (e.g., in the carotid artery) reaches the brain in less than half a minute, and an injection anywhere in the system has a delivery time of minutes. The vasculature also provides remarkable access: in the neocortex, all neural somata are within <25 microns of a blood vessel. Further, this intrinsic routing network is not subject to the uneven diffusion of injections in other body areas, or the delays and impediments of oral delivery.

However, drug delivery to the brain is impeded by the presence of the BBB. The BBB shields the brain against potentially toxic substances present in the blood stream and is crucial for normal brain function, preventing cross-talk between blood elements and neural signaling and balancing metabolic delivery.

Endothelial cells lining the blood vessels constitute the main component of the BBB. Endothelial cells (ECs) are closely sealed by tight junctions, possess few fenestrae and few endocytic vesicles as compared to capillaries of other organs. The ECs are surrounded by extracellular matrix, astrocytes, pericytes, vascular smooth muscle cells, and microglial cells. The close association of endothelial cells with the astrocyte foot processes and the basement membrane of capillaries are important for the development and maintenance of the BBB properties that permit tight control of blood-brain exchange.

The BBB presents passive and active resistance to brain permeability. The proximity of tight junctions (TJ) between brain ECs limit intercellular trans-laminar flow to small hydrophilic molecule. Those molecules that cross the EC by trans-cellular, non-receptor mediated means are lipophilic (logP~4) and low molecular weight (e.g., <400 D). However, most molecules fitting this profile do not cross the BBB because active efflux transporters, such as the permeability glycoprotein (e.g., P-gp), extrude them. Select small molecules (e.g., amino acids) are relayed by transport proteins, and a few large molecules by receptor-mediated transcytosis. Thus the BBB prevents 98% of all small-molecule therapeutics, and essentially 100% of all unmodified large-molecule therapeutics from entering the brain. Because, peptide and protein therapeutics are generally excluded from transport from blood to brain, owing to the negligible permeability of the brain capillary endothelial wall to these drugs, ECs represent the major obstacle for the use of potential therapeutics against many disorders of the CNS.

There is extensive evidence that multiple factors under optogenetic control can have a powerful impact on BBB permeability: calcium, membrane potential, chloride, and dilation. Manipulation of extracellular calcium influx profoundly impacts EC permeability. Mechanisms include manipulation of TJ width by calcium impact on cytoskeletal proteins (e.g., regulating phosphorylation). Several lines of evidence indicate EC calcium concentration also regulates P-gp mediated drug resistance. Membrane potential changes also impact permeability, effects likely mediated by P-gp modulation. The EC also possess several chloride channels, and chloride regulation has long been believed to impact BBB permeability. Regulating calcium levels, chloride levels, or membrane potential in EC should regulate EC permeability. Recent studies have also indicated that induction of vasodilation, for example driven by local neural activity in the process of functional hyperemia, can also enhance BBB permeability.

We have discovered an optogenetic method for controlling the permeability of ECs in the vasculature. In one aspect of the invention, as described in FIG. 1, the method can be used for transporting IV-delivered therapeutics across the BBB into the brain. This is achieved by system-wide expression of optogenetic elements in ECs and local presentation of light in a defined area of the brain, thus achieving spatial control of BBB regulation. These optogenetic elements include ion channels, chloride channels, and/or proton pumps, whose permeability properties are reversibly changed upon presentation of light of a specific wavelength. Light of multiple wavelengths can be used to change the permeability properties of cells between two states. Presentation of light of one wavelength (e.g., blue-green) may change EC permeability and open or close the BBB. Presentation of light of a different wavelength (e.g., yellow or amber) can have the opposite effect. For example, light of one wavelength increases EC permeability and opens the BBB and light of another wavelength decreases EC permeability and closes the BBB. Thus using light of two different wavelengths, precise temporal control in the opening and closing the BBB can be achieved. The invention provides a non-invasive and simple method for regulating the BBB, uses conventional drug delivery methods such as IV-injection, and is a viable long-term option where repeated opening and closing of the BBB may be required over a long course of treatment.

Optogenetic Reagents

The invention discloses the use of optogenetic reagents which includes ion channels, chloride channels, and proton pumps. These include channelrhodopsins, halorhodopsins, archaerhodopsins, or melanopsins, their natural variants, engineered chimeras or variants, and humanized variants as described in Table 1.

In one aspect of the invention, each of the channels described below is also modified by addition of recombinant endoplasmic reticulum export and trafficking signal for improved cell surface expression.

In one aspect of the invention, the optogenetic reagent is a channelrhodopsin, e.g., ChR1, ChR2, VChR1, ChR2 C128A, ChR2 C128S, ChR2 C128T, ChD, ChEF, ChF, or ChIEF. Channelrhodopsins (ChRs) are light-gated ion channels originating from microalgae. The Vitamin A derivative retinal is linked to a lysine residue of the proteins (Retinal Schiff Base, RSB) constituting the light absorbing chromophore. They are activated by blue light. The blue light can have a wavelength of approximately 470 nm (e.g., 440, 450, 460, 470, 480, 490 nm). Light absorption causes retinal isomerization around the 13-bond. This isomerization triggers subsequent conformational changes of the protein and gating of the channel. Thermal relaxation of the proteins closes the channel and the protein converts under re-isomerization of the retinal back to the dark state.

ChR2 from *Chiamydomonas reinhardtii* has been established as the ChR prototype for optogenetic application since it is more than 10 times better expressed in most host cells than the earlier found ChR1. In one aspect of the invention, the channelrhodopsin is vChR1 or vChR2 derived from *Volvox carteri*. Variants of channelrhodopsins are listed below in Table 1.

In one aspect of the invention, the channelrhodopsin is a humanized ChR2 with two mutations (E123T and H134R), and is called ChETA. ChETA has faster deactivation kinetics and faster recovery from inactivation.

In another aspect of the invention, the channelrhodopsin is a step function opsin (SFO) with bi-stable excitation that is engineered by a point mutation of ChR2, e.g., ChR2C128A, ChR2C128, and ChR2C128T. Each of these channels is opened by presenting blue light (470 nm) and the channels can be closed by shining a pulse of green light (542 nm). SFOs allow opening and closing the channel by shining light of different wavelengths, thus providing precise temporal control over the permeability of endothelial cells and of the BBB.

In another aspect of the invention, the channelrhodopsin is a stabilized step-function opsin (SSFO) that is engineered by making two mutations in ChR2 (C128S and D156A). The SSFO channel has a more stabilized conducting state with a time constant of nearly 30 minutes following a brief pulse of activating light. The SSFO may be closed using yellow light (590 nm).

In another aspect of the invention, the optogenetic reagent is a halorhodopsin, e.g., NpHR, eNpHR 2.0, and eNpHR 3.0. Halorhodopsins are light-gated chloride channels originating from halobacteria and are activated by yellow (or amber) light of approximately 570 nm wavelength (e.g., 540, 550, 560, 570, or 580 nm). The halorhodopsin from *Natronomonas pharaonis* (NpHR) has been established as the prototype halorhodopsin and has been used for engineering the variants eNpHR 2.0 (Gradinaru et al., *Brain Cell Biol.*, 2008, 36 (1-4): 129-139, incorporated herein by reference) and eNpHR 3.0 (Gradinaru et al., *Cell*, 2010, 141 (1):154-165, incorporated herein by reference) described in Table 1.

In one aspect of the invention, the halorhodopsin is eNpHR 2.0 made by fusion of the FCYENEV ER export motif from a vertebrate inward rectifier potassium channel to the C-terminus of the NpHR protein. In another aspect of the invention, the halorhodopsin is eNpHR 3.0 made by adding the trafficking signal from Kir2.1 to the C terminus of the NpHR protein.

TABLE 1

| Channel Acronym | Name of channel | Organism from which channel was isolated | Peak Excitation Wavelength (nm) | Type of Channel | Open/Close |
| --- | --- | --- | --- | --- | --- |
| ChR1 | Channelrhodopsin1 | *Clamydomonas reinhardti* | 470 | Ion channel (H+, Na+, K+, Ca2+) | Open by blue light |
| ChR2 | Channelrhodopsin2 | *Clamydomonas reinhardti* | 470 | Ion channel (H+, Na+, K+, Ca2+) | Open by blue light |
| vChR1 | Channelrhodopsin1 | *Volvox carteri* | 570 | Ion channel (H+, | Open by yellow light |

TABLE 1-continued

| Channel Acronym | Name of channel | Organism from which channel was isolated | Peak Excitation Wavelength (nm) | Type of Channel | Open/Close |
|---|---|---|---|---|---|
| vChR2 | Channelrhodopsin2 | *Volvox carteri* | 470 | Ion channel (H+, Na+, K+, Ca2+) | Open by blue light |
| ChR2H134R | Channelrhodopsin2 (mutant) | *Clamydomonas reinhardti* | 450 | Ion channel (H+, Na+, K+, Ca2+) | Open by blue light |
| ChR2E123T (ChETA) | Channelrhodopsin2 (mutant) | *Clamydomonas reinhardti* | 490 | Ion channel (H+, Na+, K+, Ca2+) | Open by blue light (faster deactivation) |
| ChD | Channelrhodopsin ½ hybrid | *Clamydomonas reinhardti* | 450 | Ion channel (H+, Na+, K+, Ca2+) | Open by blue light |
| ChEF | Channelrhodopsin ½ hybrid | *Clamydomonas reinhardti* | 470 | Ion channel (H+, Na+, K+, Ca2+) | Open by blue light |
| ChIEF | Channelrhodopsin ½ hybrid | *Clamydomonas reinhardti* | 450 | Ion channel (H+, Na+, K+, Ca2+) | Open by blue light |
| ChR2C128A | Channelrhodopsin2 (mutant) | *Clamydomonas reinhardti* | 470(open)/ 542(close) | Ion channel (H+, Na+, K+, Ca2+) | Step function (open by blue light and close by yellow light) |
| ChR2C128S | Channelrhodopsin2 (mutant) | *Clamydomonas reinhardti* | 470(open)/ 542(close) | Ion channel (H+, Na+, K+, Ca2+) | Step function (open by blue light and close by yellow light) |
| ChR2C128T | Channelrhodopsin2 (mutant) | *Clamydomonas reinhardti* | 470(open)/ 542(close) | Ion channel (H+, Na+, K+, Ca2+) | Step function (open by blue light and close by yellow light) |
| NpHR | Halorhodopsin | *Natromonas pharaonis* | 570 | Chloride | Open by yellow light for inhibition |
| eNpHR 2.0 | engineered Halorhodopsin | *Natromonas pharaonis* | 570 | Chloride | Open by yellow light for inhibition |
| eNpHR 3.0 | engineered Halorhodopsin | *Natromonas pharaonis* | 570 | Chloride | Open by yellow light for inhibition |
| Arch 3.0 | Archaerhodopsin | *Halorubrum sodomense* | yellow light | Proton pump | Open by yellow light for inhibition |
| Arch T 3.0 | Archaerhodopsin | *Halorubrum sodomense* | yellow light | Proton pump | Open by yellow light for inhibition |
| Mac 3.0 | Outward light-gated proton pump | *Leptosphaeria maculans* | 542 | Proton pump | Open by yellow light for inhibition |

In another aspect of the invention, the optogenetic reagent is an archaerhodopsin, e.g., Arch, Arch T, and Arch T 3.0. Archaerhodopsins are light-driven proton pumps from the archaebacteria *Halorubrum sodomense*, e.g., Arch and are activated by yellow light. In yet another aspect of the invention, the optogenetic reagent is Arch T is derived from the *Halorubrum* sp. TP009 strain and is 3.5 times more sensitive than Arch.

In another aspect of the invention, the optogenetic reagent is Mac3.0 and is an outward light-gated proton pump from *Leptosphaeria maculans*, also activated by yellow light.

In one aspect of the invention, a channelrhodopsin can be coexpressed with a halorhodopsin to achieve bidirectional control of cell membrane permeability as described in Zhang et al (Zhang et al., *Nature*, 2007, 446 (7136):633-639, incorporated herein by reference).

Genetic Means for Delivery of Optogenetic Reagents in to Cells

The optogenetic reagents used in the present invention can be expressed in endothelial cells or its precursors by delivery of recombinant nucleic acid molecules encoding these reagents into the cells. The recombinant nucleic acid molecules are cloned into appropriate expression vectors that contain regulatory elements necessary for expression of the optogenetic reagents. The recombinant nucleic acid molecules can be delivered into cells by any one or more methods known in the art e.g., by a virus, by electroporation, by liposomes, or by transgenic methods. These are described below.

Expression Vectors Containing Recombinant Nucleic Acid Molecule for Expressing Optogenetic Reagents in Cells The invention features recombinant nucleic acid molecules encoding the optogenetic reagents that are cloned into expression vectors. These expression vectors, and the regulatory sequences used for expression of optogenetic reagents are described below.

Construction of vectors for recombinant expression of optogenetic reagents for use in the invention may be accomplished using conventional techniques which do not require detailed explanation to one of ordinary skill in the art. For review, however, those of ordinary skill may wish to consult Maniatis et al., in Molecular Cloning: A Laboratory Manual, Cold Spring Harbor Laboratory (NY 1982).

For generation of efficient expression vectors, it is necessary to have regulatory sequences that control the expression of the optogenetic reagent. These regulatory sequences include promoter and enhancer sequences and are influenced by specific cellular factors that interact with these sequences.

Promoter and enhancer regions have been described in the art. Methods for maintaining and increasing expression of transgenes in quiescent cells include the use of promoters including collagen type I (1 and 2), SV40, and LTR promoters. According to one embodiment of the invention, the promoter is a constitutive promoter selected from the group consisting of: ubiquitin promoter, CMV promoter, JeT promoter (e.g., as described in U.S. Pat. No. 6,555,674, incorporated herein by reference), SV40 promoter, Elongation Factor 1 alpha promoter (EF1-alpha), RSV, Mo-MLV-LTR. Examples of inducible/repressible promoters include: Tet-On, Tet-Off, Rapamycin-inducible promoter, and Mx1.

In another embodiment of the invention, the promoter is constitutive or inducible endothelial cell specific promoter selected from the group consisting of: a family of receptor tyrosine kinase genes specifically expressed in mammalian endothelial cells, including Tie1 and Tie2 (also called Tek) (Dumont et al., *Oncogene*, 7: 1471-1480, 1992; Schnurch and Risau, *Development*, 119: 957-968, 1993), fms-like tyrosine kinase-1 (FLT-1) (Nicklin et al., *Hypertension*, 38: 65-70, 2001), intercellular adhesion molecule 2 (ICAM-2) (Cowan et al., *Transplantation*, 62: 155-160, 1996), VE-cadherin (VECD) (Hisatsune et al., *Blood*, 105: 4657-4663, 2005), Endothelial cell-specific molecule 1 (ESM1) (Lassalle et al., *J. Biol. Chem.* 271: 20458-20464, 1996) and synthetic variants thereof.

In addition to using viral and non-viral promoters to drive transgene expression, an enhancer sequence may be used to increase the level of transgene expression. For example, in the present invention collagen enhancer sequences may be used with the collagen promoter 2 (I) to increase transgene expression. In addition, the enhancer element found in SV40 viruses may be used to increase transgene expression. This enhancer sequence consists of a 72 base pair repeat as described by Gruss et al., *Proc. Natl. Acad. Sci. USA*, 1981, 78: 943; Benoist and Chambon, *Nature*, 1981, 290: 304, and Fromm and Berg, *J. Mol. Appl. Genetics*, 1982, 1: 457, each of which is incorporated herein by reference. This repeat sequence can increase the transcription of many different viral and cellular genes when it is present in series with various promoters (Moreau et al., *Nucleic Acids Res.*, 1981, 9: 6047, incorporated herein by reference).

Further expression enhancing sequences include but are not limited to Woodchuck hepatitis virus post-transcriptional regulation element, WPRE, SP163, CMV enhancer, and Chicken β-globin insulator or other insulators.

Transgene expression may also be increased for long term stable expression using cytokines to modulate promoter activity. Several cytokines have been reported to modulate the expression of transgene from collagen 2 (I) and LTR promoters. For example, transforming growth factor (TGF), interleukin (IL)-I, and interferon (INF) down regulate the expression of transgenes driven by various promoters such as LTR. Tumor necrosis factor (TNF) and TGF 1 up regulate, and may be used to control, expression of transgenes driven by a promoter. Other cytokines that may prove useful include basic fibroblast growth factor (bFGF) and epidermal growth factor (EGF).

Collagen promoter with the collagen enhancer sequence (Coll (E)) may also be used to increase transgene expression by suppressing further any immune response to the vector which may be generated in a treated brain notwithstanding its immune-protected status. In addition, anti-inflammatory agents including steroids, for example dexamethasone, may be administered to the treated host immediately after vector composition delivery and continued, preferably, until any cytokine-mediated inflammatory response subsides. An immunosuppression agent such as cyclosporin may also be administered to reduce the production of interferons, which downregulates LTR promoter and Coll (E) promoter-enhancer, and reduces transgene expression.

The expression vector may further comprise sequences such as a sequence coding for the Cre-recombinase protein, and LoxP sequences. A further way of ensuring temporary expression of the optogenetic reagent is through the use of the Cre-LoxP system which results in the excision of part of the inserted DNA sequence either upon administration of Cre-recombinase to the cells or by incorporating a gene coding for the recombinase into the virus construct. Incorporating a gene for the recombinase in the virus construct together with the LoxP sites and a structural gene (an optogenetic reagent in the present case) often results in expression of the structural gene for a period of approximately five days or more.

Virus Mediated Delivery of Expression Vectors to Express Optogenetic Reagents in Endothelial Cells In one aspect of the invention, the expression vector containing the recombinant nucleic acid encoding the optogenetic reagent is encapsidated within a recombinant virus e.g., recombinant adeno-associated virus (AAV), recombinant retrovirus, recombinant lentivirus, recombinant poxvirus, recombinant rabies virus, recombinant pseudo-rabies virus, and recombinant herpes simplex virus, papovavirus, human immunodeficiency virus (HIV), and adenovirus. These viruses are then applied to the subject (e.g., a patient) so that the endothelial cells can be infected by these viruses and the optogenetic reagents can then be expressed in endothelial cells.

Preferred viruses include lentiviruses and adeno-associated viruses (AAVs). Both types of viruses can integrate into the genome without cell divisions, and both types have been tested in pre-clinical animal studies. Methods for preparation of AAVs are described in the art e.g., in U.S. Pat. No. 5,677,158, U.S. Pat. No. 6,309,634, and U.S. Pat. No. 6,683,058, each of which is incorporated herein by reference. Methods for preparation and in vivo administration of lentiviruses are described in U.S. No. 20020037281 (incorporated herein by reference). Preferably, a lentivirus vector is a replication-defective lentivirus particle. Such a lentivirus particle can be produced from a lentiviral vector comprising a 5' lentiviral LTR, a tRNA binding site, a packaging signal, a promoter operably linked to a polynucleotide signal encoding said fusion protein, an origin of second strand DNA synthesis and a 3' lentiviral LTR.

Retroviruses are most commonly used in human clinical trials, since they carry 7-8 kb and since they have the ability to infect cells and have their genetic material stably integrated into the host cell with high efficiency (see, e.g., WO 95/30761; WO 95/24929, each of which is incorporated herein by reference). Oncovirinae require at least one round of target cell proliferation for transfer and integration of exogenous nucleic acid sequences into the patient.

For use in human patients, the retrovirus must be replication defective. This prevents further generation of infectious retroviral particles in the target tissue. Instead the replication defective virus becomes a "captive" transgene stable incorporated into the target cell genome. Typically in replication defective vectors, the gag, env, and pol genes have been deleted (along with most of the rest of the viral genome). Heterologous DNA (in case of the present invention, the recombinant nucleic acid molecule encoding the optogenetic reagent) is inserted in place of the deleted viral genes. The heterologous genes may be under the control of the endogenous heterologous promoter, another heterologous promoter active in the target cell, or the retroviral 5' LTR (the viral LTR is active in diverse tissues).

In one embodiment, the viruses are introduced into the body by intravascular injection. For localized targeting, virus injection from an IV catheter has already been used to achieve spatially discrete expression (e.g., of a single chamber of the heart or localized cerebral vasculature). In cases where the desired target can be accessed by catheterization, local transduction would then provide spatial specificity to BBB opening. Alternatively, direct intra-cerebral virus injection can be used to target specific vessels. While more invasive than catheterization, this procedure is less invasive than implantation of a deep-brain stimulator and does not require maintenance of hardware in the brain. Further, in cases where more elaborate surgery is already standard—tumor removal, epilepsy surgery—local transduction could be achieved. Alternatively, direct peripheral virus injection can be used to target specific vessels outside of the central nervous system.

Viruses encoding optogenetic reagents may be placed into a pharmaceutically acceptable suspension, solution or emulsion. Suitable mediums include saline and liposomal preparations. More specifically, pharmaceutically acceptable carriers may include sterile aqueous of non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like.

Non-Viral Methods for Delivery of Expression Vectors to Express Optogenetic Reagents in Endothelial Cells The recombinant nucleic acid molecule encoding the optogenetic reagent may be delivered into ECs by non-viral methods. For example, a colloidal dispersion system may be used for targeted gene delivery. Colloidal dispersion systems include macromolecule complexes, nanocapsules, microspheres, beads, and lipid-based systems including oil-in-water emulsions, micelles, mixed micelles, and liposomes. Liposomes are artificial membrane vesicles that are useful as delivery vehicles in vitro and in vivo. It has been shown that large unilamellar vesicles (LUV), which range in size from 0.2-4.0 µm, can encapsulate a substantial percentage of an aqueous buffer containing large macro molecules. RNA, DNA and even intact virions can be encapsulated within the aqueous interior and be delivered to cells in a biologically active form. For a liposome to be an efficient gene transfer vehicle, the following characteristics should be present: encapsulation of the expression vector at high efficiency while not compromising their biological activity; preferential and substantial binding to a target cell in comparison to non-target cells; delivery of the aqueous contents of the vesicle to the target cell cytoplasm at high efficiency; and accurate and effective expression of genetic information.

The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations. Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Particularly useful are diacylphosphatidylglycerols, where the lipid moiety contains from 14-18 carbon atoms, particularly from 16-18 carbon atoms, and is saturated. Illustrative phospholipids include egg phosphatidylcholine, dipalmitoylphosphatidylcholine and distearoylphosphatidylcholine.

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticulo-endothelial system (RES) in organs which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted gene delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand.

Fiducial Markers

Since the optogenetic reagents cannot be visualized within cells, it is useful to have fiducial markers that can provide information on whether endothelial cells received the recombinant nucleic acid molecule encoding the optogenetic reagent and whether the optogenetic reagent may be expressed in these cells. This is achieved by using fluorescent fiducial marker proteins well known in the art, e.g., green fluorescent protein (GFP), red fluorescent protein (RFP), yellow fluorescent protein (YFP), and their natural and engineered variants. When expressed in cells, and when contacted with the correct wavelength of light, these proteins produce a fluorescent signal that can be visualized.

In one aspect of the invention, the fiducial marker is co-expressed with the optogenetic reagent. This can be achieved by using two promoters in the expression vector. One promoter drives the expression of the optogenetic reagent, while the other promoter drives the expression of the fiducial marker protein. It is well accepted in the art that the expression of the fiducial marker protein is an indication that the optogenetic reagent is also expressed in the same cell. The two promoters can be of the same kind or of different kinds. For example, a CMV promoter can drive the expression of the optogenetic reagent, while an EF1-α promoter may drive expression of the fiducial marker. Alternatively both promoters can be CMV promoter.

In one aspect of the invention, the fiducial marker gene is cloned in the same reading frame as the optogenetic element coding gene with an internal ribosome entry site (IRES) in between the two open reading frames (ORFs). The IRES enables the co-translation of the fiducial marker protein from the same mRNA that encodes the optogenetic reagent, thus producing two separate proteins. Alternatively, the IRES sequence can be replaced by the 2A sequence known in the art. The 2A protein is a self cleaving peptide that when translated cleaves and releases the protein translated downstream of it. Thus the fiducial marker protein is translated and then released. In both of these methods the expression of the fiducial marker protein provides confirmation of the expression of the optogenetic reagent.

In another aspect of the invention, the fiducial marker gene is cloned as a fusion protein with the optogenetic reagent. Typically, a fiducial marker protein is fused to the C-terminus (cytoplasmic side) of the optogenetic reagent.

Light Sources and Delivery of Light for Regulating Permeability of Cells Expressing Optogenetic Reagents Light Source The permeability of ECs expressing the optogenetic reagents can be changed by presentation, to these cells, of light of the appropriate wavelength. The source of the light can be one or more of a laser e.g., a diode-pumped solid-state laser. Alternatively the light source can be one or more of a light emitting diode (LED), or an array of LEDs emitting light of a specific wavelength (Zorzos et al, *Optics Letters,* 2010, 35:24, 4133; and in Bernstein et al, *Proc. Soc. Photo Opt. Instrum. Eng.,* 2008, 6854:68540H, each of which is incorporated herein by reference). In one aspect of the invention, the light source can be an array of multi-wavelength LEDs as described in Bernstein et al, 2008, for presenting light of different wavelengths. Additionally, shutters and filters can be used to control the duration and wavelength of light.

Light Delivery

The invention features delivery of light using optical fibers. This approach typically involves the use of a cannula that is implanted on the area of the body, e.g., brain, where light will be presented. The cannula allows for precise targeting of the optical fiber. The optical fiber can be connected to a laser via a FC/PC connection. Typically the optical fibers are placed using stereotactic guidance to deliver light to a precise location.

In another aspect of the invention, light can be delivered through a multi-waveguide implantable probe that can deliver light of multiple wavelengths, e.g., blue and yellow light, to multiple target areas along the axis of the probe. The design of such a probe is described in detail in Zorzos et al, supra. Such a probe is useful for delivering light of two different wavelengths to precise areas of the vasculature and ECs to drive optogenetic reagents, e.g., step function opsins, thus providing precise spatial and temporal control of when and where EC permeability is changed.

In yet another aspect of the invention, light can be delivered using an implantable prosthetic device containing 4D-LED arrays as described in Bernstein et al, supra. Such a device does not use an expensive and bulky laser setup, and can be designed as a prosthetic device that can be attached to a part of the body, e.g., the brain, for delivery of light. In addition, 4D LED arrays allow the delivery of multiple wavelengths of light thus providing precise temporal and spatial control of regulating the permeability of ECs.

In one aspect of the invention, light may be delivered using a light delivery catheter as described in U.S. Pat. No. 6,290,668, incorporated herein by reference. Such catheters contain a guidewire and a light guide and are approved for therapeutic uses, e.g., removal of blood clots. With this approach, the BBB could be locally controlled at the site of positioning of the fiber optic or fiber optics without surgical implantation or presentation of a fiber optic, making spatiotemporally localized control of the BBB relatively less invasive.

In another aspect of the invention, light may be provided by a bioluminescent reaction. We and others (Berglund et al., *PLoS One,* 8:e59759, 2013; incorporated herein by reference) have shown that bioluminescent enzymes (commonly referred to by the name 'luciferases') can, in the presence of their required co-factor (small molecules commonly referred to by the name 'luciferins'), generate sufficient photon production to drive robust optogenetic reactions. Luciferases can be expressed in the same endothelial cell as the optogenetic elements or in other cells or vehicles to create the desired control of endothelial physiology for the impact(s) described throughout the application. Luciferases dependent on other co-factors beyond luciferin presentation—such as the well-described calcium dependence of the Aequorin enzyme—can also be employed to allow activity-dependent regulation of endothelial physiology. Fusion proteins tethering optogenetic elements to bioluminescent enzymes (referred to as 'luminopsins' in Berglund et al., 2013, supra) can also be employed, as can many other combinations that place these two factors in sufficient proximity. Delivery of luciferins can occur through intravenous injection, through direct infusion by a cannula, or through other methods. These small molecules can in many instances cross the blood-brain barrier, removing a barrier to application.

The use of this specific mode of light production allows the control of endothelial cells repeatedly through minimally invasive intravenous delivery. For example, if the vasculature surrounding a tumor were made to express luciferases and optogenetic elements, then at a later date intravenous injection of an anti-tumor agent with a luciferin facilitates delivery across the blood-brain barrier to enhance the concentration of drug reaching the desired target. In another application, expression of such a combination of luciferase and optogenetic elements allows for the continued induction of vasoconstriction in the region of a tumor, potentially negatively impacting the tumor by reducing perfusion to it acutely, or through impairing angiogenesis.

Therapeutic Uses of the Invention

The invention features methods for controlling endothelial cells and uses of these methods for treating disorders where control of vascular properties is involved. For example, control of EC permeability provides a method of controlling vascular permeability in the brain, e.g., by controlling the blood-brain barrier, (BBB), or in the rest of the body (e.g., by controlling the blood-lung barrier). This control may either be exerted locally (e.g., in a single brain area) or globally (e.g., throughout the brain or even the entire body). Control of EC permeability may be used to facilitate delivery, from the blood to other tissues, of exogenous elements including drugs, cells, molecules, antibodies, and organic and inorganic compounds. Additionally, EC permeability can be manipulated to block or decrease delivery of such exogenous substances. Control of EC permeability may also be used to facilitate the delivery from the blood to other tissues of endogenous elements such as hormones, nutrients, precursors in biochemical processes (e.g., amino acids that will be converted to neurotransmitters in the central nervous system) and cells (e.g., immune cells). Additionally, EC permeability can be used to block or decrease delivery of such endogenous elements. With tight optogenetic control over the BBB or other EC mediated barriers, opening and then closing it with precision will allow higher drug concentration to be delivered to the permeabilized area with lower IV infusion concentration (FIG. 1). Optogenetic vascular barrier opening could be achieved minimally invasively by catheterized fiber optics. Alternatively, intracranial fiber optic implantation is no more invasive than the approaches currently used.

Therapeutic Uses in Treatment of Brain Disorders

The invention features methods that can facilitate the delivery of therapeutics (e.g., drugs, small molecules, peptides, proteins, antibodies, nucleic acid molecules, and organic and inorganic compounds) to the brain, across the BBB, to treat brain disorders. For example, the BBB is a key challenge in neuro-oncology. Glioma prognosis (80% of malignant diagnoses) is poor. Glioblastoma multiforme, the most common glioma, shows ~18 month life expectancy.

Other diseases in which changes in BBB permeability could enhance delivery of exogenous therapeutics include brain cancer, epilepsy, Parkinson's disease, Alzheimer's disease, neurological diseases of other types, and psychiatric diseases (e.g., by selective delivery of anti-depressants to relevant brain regions and not other unintended targets).

In case of several diseases, control of BBB permeability to endogenous factors could improve disease outcomes. For example, inappropriate permissiveness of the BBB is a major source of several brain diseases including Alzheimer's Disease (AD), Multiple Sclerosis (MS), malaria, and meningitis, all of which show inappropriate transmission across the BBB. In AD, amyloid-β accumulation in the brain is believed to result from increased influx across EC and/or decreased efflux after brain accumulation. Enhancing the BBB could be beneficial in AD, and in case of the present invention—which selectively targets EC and can be made to span the entire vasculature non-invasively—is advantageous. The targeted variants of the present invention could also be useful in MS, which shows a localized failure in barrier properties and is treated by blockade of leukocyte permeability. Increased blockade at the site of lesion can be increased and could potentially enhance the BBB only at that position, allowing its normal function in the rest of the BBB.

Therapeutic Uses in Control of Vascular Tone and Arterial Diameter

Control of ECs can be used to control vascular tone and directly linked phenomena such as blood flow rate, blood volume, and blood pressure, including direct induction of vasoconstriction or vasodilation. In one aspect of the invention, the method provides bi-directional control of vessel resistivity to manipulation by other sources and can help in prevention or decrease of constriction or dilation by endogenous factors in the body (e.g., that occur as a symptom of a disease), or by exogenous factors administered (e.g., blocking the vascular impact of a drug that has a different therapeutic target).

In another aspect of the invention, the method provides a way for the enhancement of constriction or dilation by endogenous factors in the body (e.g., promoting metabolism-driven dilation/hyperemia) or exogenous factors administered (e.g., potentiating the efficacy of blood-pressure medication). Several medical conditions and/or diseases enhance or diminish the natural capacity to control blood flow, volume and/or pressure, or the ability to maintain vascular tone. In the extreme, damage in most strokes and aneurysms may be considered such problems, and a host of other diseases including diabetes, hypertension, varicose veins, erectile dysfunction, and variants of cardiac disease fit this description. As such, the ability to control vascular tone is a major therapeutic target. Further, the delivery of blood-borne factors (e.g., exogenous or endogenous agents) could also be enhanced or retarded by increased blood flow and/or volume to a region, thereby enhancing drug delivery and/or nutrient supply. Also, this application of vascular control could be introduced for acute treatment contexts, such as anticipated need for reducing blood flow to a region during surgery. In this application, patients would be pre-treated with manipulations that achieve EC optogenetic expression, so that light could be used in the procedure. Another such relevant application would be in advance of individuals anticipating potential injury (e.g., soldiers), where achieving control over vascular tone with light could allow more efficient treatment in potentially adverse contexts (e.g., a battlefield).

Therapeutic Uses in Control of Vascular Growth

In yet another aspect of the invention, optogenetic control of ECs provides a means of manipulating ECs to control vascular growth and retraction in any part of the body. Several diseases, including stroke, cerebrovascular epilepsies, retinopathies (e.g., macular degeneration) and cancer, are typified by maladaptive growth of vasculature (angiogenesis). Conversely, several diseases are characterized by insufficient ingrowth e.g., into ischemic tissue zones. Perturbation of EC is known to promote or retard such vascular growth depending on the nature of the stimulation. As such, regulation of EC physiology by direct and likely repeated activation or inactivation through optogenetic means could provide a direct means for retarding or stimulating vascular elaboration.

Therapeutic Uses in Treatment of Lung Cancer

The methods described above, for the brain, will provide general infrastructure/methods for innovations in delivery across, or reinforcement of, the blood-lung barrier. As one example, optogenetic regulation of EC membrane properties in the lung could improve efficacy and targeting of adjuvant chemotherapy to improve drug penetration in non-small cell lung carcinoma.

EXAMPLES

Example 1: Modulation of EC Permeability in the BBB Using Halorhodopsin-3.0

Figure 2A:
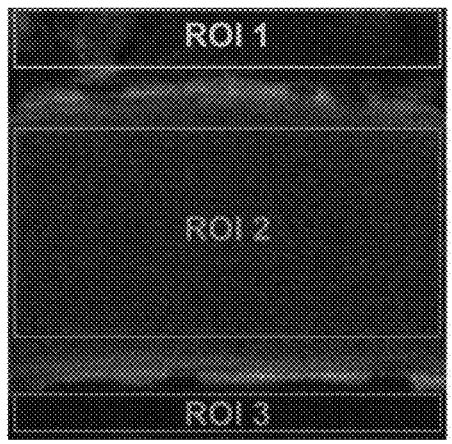
FIG. 2A is a micrograph obtained by 2-photon imaging of a mouse brain expressing optogenetic reagents in ECs. A brief optogenetic drive of Halohodopsin-3.0 (Halo), a photo-activated chloride pump can open the BBB and let rhodamine-dextran enter from the blood into the brain. Three different regions of interest (ROI's) have been marked for quantification of the rhodamine fluorescence that entered the brain as a result of the opening of the Halorhodopsin channel.
Figure 2B:
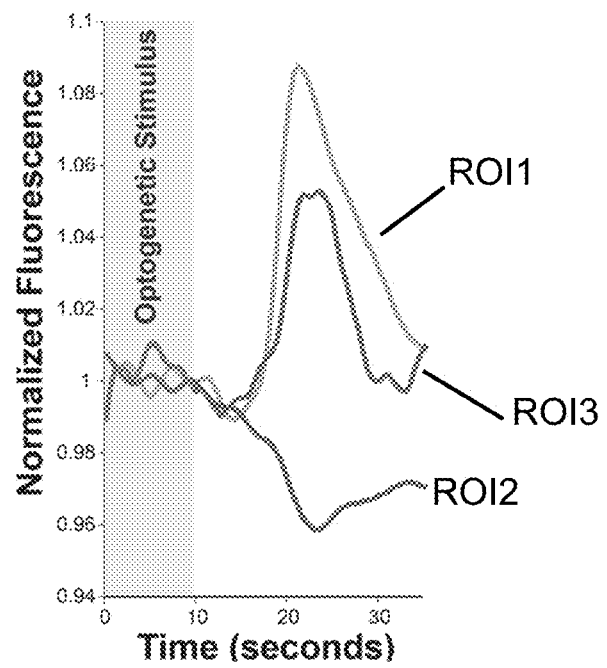
FIG. 2B is a graph showing the quantification of the florescence in the three ROIs marked in FIG. 2A. The X-axis shows the time and the Y-axis shows the fluorescence of rhodamine-dextran in each of the three ROIs.

Halorhodopsin-3.0 was selectively expressed in mouse ECs using IV viral injection. After ~6 weeks, 2-photon imaging of the in vivo neocortex (a still image is shown in FIG. 2A) was used to test the impact of optogenetic stimulation on the BBB. To measure extravasation, rhodamine-dextran (10 kD), which does not typically cross the BBB, was injected via IV. Amber light pulses (optimized for Halorhodopsin) were presented for 10 seconds. Following stimulation, a discrete increase in fluorescence in neocortex surrounding the vessel occurred (ROIs 1 and 3/time series) with a decrease in intra-arterial emission (ROI2), indicating movement of rhodamine-dextran across the BBB into the brain (Please see FIG. 2A and FIG. 2B). Vessel walls were stationary throughout, and control experiments in non-transduced mice did not show these effects. This BBB opening was discrete in time, <15 seconds.

Example 2: Second Example of Modulation of EC Permeability in the BBB Using Halorhodopsin-3.0

Halorhodopsin-3.0 was selectively expressed in mouse ECs using transgenic mice bred to encode Cre-recombinase in ECs, and LoxP sequences flanking the fusion protein Halorhodopsin (eNpHR 3.0)-Enhanced Yellow Fluorescent Protein (Halo3.0-EYFP).

Figure 3A:
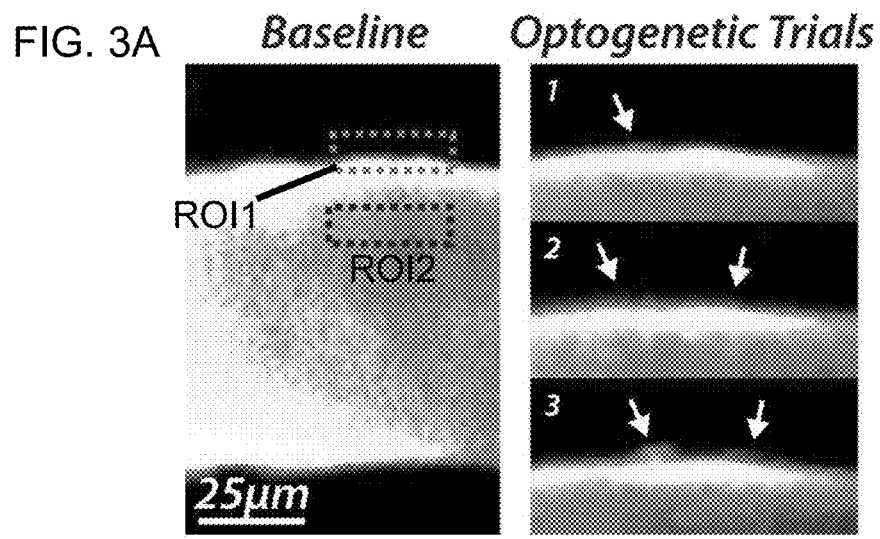
FIG. 3A is a second example of a micrograph obtained by 2-photon imaging of a mouse brain expressing optogenetic reagents in ECs. Three trials, tens seconds in duration, of brief optogenetic drive of Halorhodopsin-3.0 (Halo), a photo-activated chloride pump can open the BBB and let rhodamine-dextran enter from the blood into the brain. Two different regions of interest (ROI's) have been marked for quantification of the rhodamine fluorescence that entered the brain as a result of the opening of the Halorhodopsin channel for each trial. Arrows indicate visible rhodamine fluorescence in multiple locations outside of the BBB.
Figure 3B:
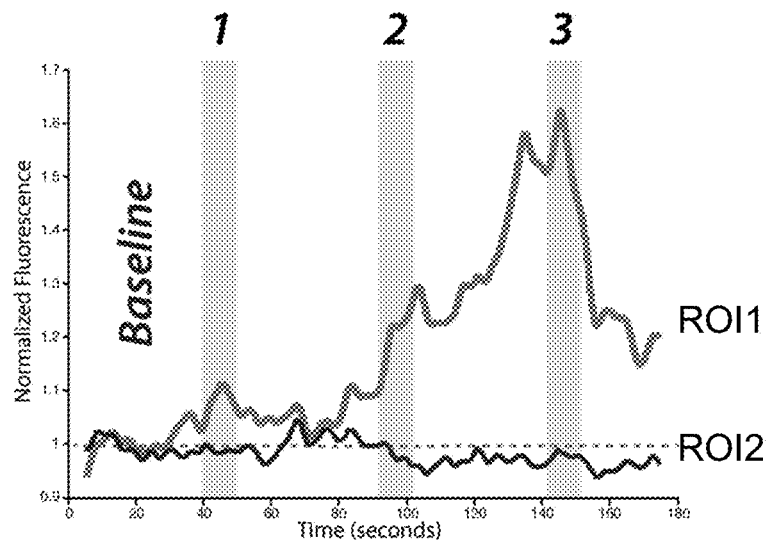
FIG. 3B is a graph showing the quantification of the florescence in the two ROIs marked in FIG. 3A. The X-axis shows the time for three trials and the Y-axis shows the fluorescence of rhodamine-dextran in each of the two ROIs.

After ~6 weeks, 2-photon imaging of the in vivo neocortex (a still image is shown in FIG. 3A) was used to test the impact of optogenetic stimulation on the BBB. To measure extravasation, rhodamine-dextran (10 kD), which does not typically cross the BBB, was injected via IV. Amber light pulses (optimized for Halorhodopsin) were presented for 10 seconds. Following stimulation (three independent presentations of the light), a discrete increase in fluorescence in neocortex surrounding the vessel occurred (ROIs 1/time series) with a small decrease in intra-arterial emission on trials 2 and 3 (ROI 2), indicating movement of rhodamine-dextran across the BBB into the brain (FIG. 3A and FIG. 3B).

Example 3: Naturally-Occurring Changes in Vascular Width

The fusion protein Channelrhodopsin-2-Enhanced Yellow Fluorescent Protein (Ch2R-EYFP) was selectively expressed in mouse ECs using transgenic mice bred to encode Cre-recombinase in ECs, and LoxP sequences flanking the fusion protein Channelrhodopsin-2-Enhanced Yellow Fluorescent Protein (Ch2R-EYFP).

Figure 4A:
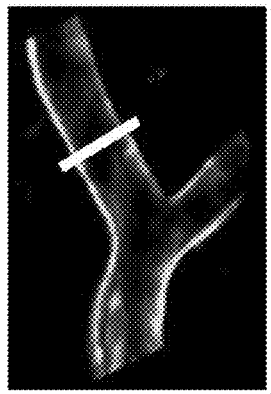
FIG. 4A and FIG. 4B are micrographs obtained using 2-photon microscopy of a mouse arteriole that is laterally coursing from approximately the border of neocortical layers I and II (bar=80 microns). The arteriole in FIG. 4A is dilated following vibrissal stimulation. The arteriole in FIG. 4B is constricted following sensory drive.
Figure 4C:
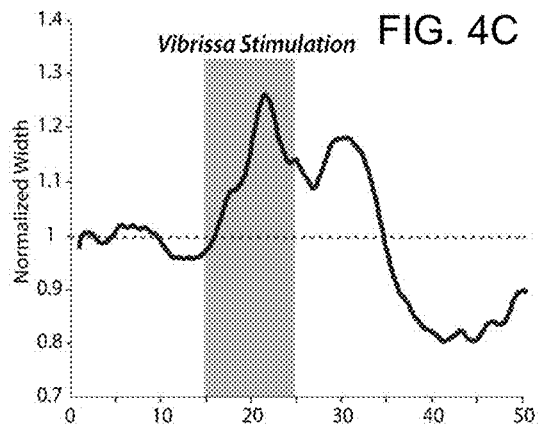
FIG. 4C and FIG. 4D are graphs showing the quantification of the normalized width of an arteriole in FIG. 4A and FIG. 4B, respectively. The X-axis shows the time, and the Y-axis shows the normalized width of the arteriole. The vibrissal stimulation is demarcated with a gray background.
Figure 4B:
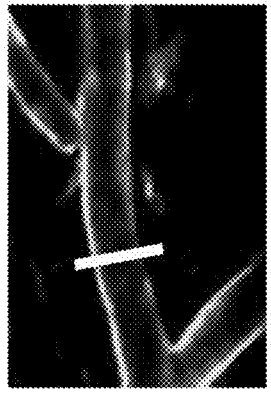
Figure 4D:
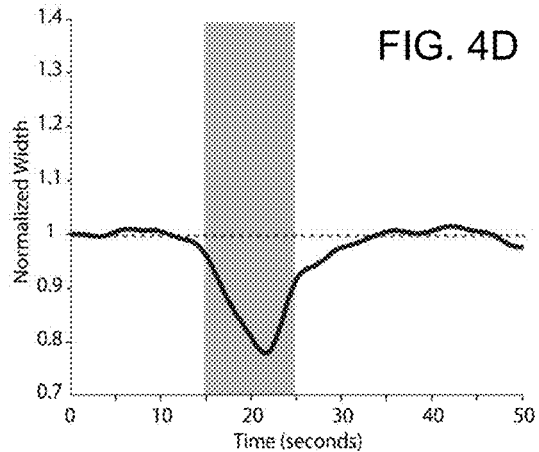

Observation of fluorescence using 2-photon microscopy confirmed the expression of Ch2R-EYFP in endothelial cells of a mouse arteriole localized above the primary sensory neocortical representation of the vibrissae ("whiskers") on the face of the mouse (FIG. 4A and FIG. 4B). The mouse vibrissae were stimulated by brief deflections applied at 5 Hz for 10 seconds. As is typical in our data, within hundreds of milliseconds of vibrissal deflection, a vascular width change is observed (FIG. 4A and FIG. 4C). In this case, the width change was a dilation that sustained for ~20 seconds. As shown in FIG. 4D, vascular constriction can be another observed vascular response to sensory drive. Not pictured are examples that are commonly observed in which natural dilations or constrictions are followed by large 'rebound' or 'overshoot' width changes in the opposite direction to that induced with sensory drive.

Example 4: Control of Vascular Dilation with Endothelial Optogenetic Drive

Figure 5A:
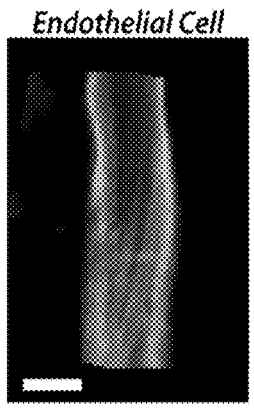
FIG. 5A is a micrograph obtained using 2-photon microscopy of a mouse arteriole labeled with EYFP.
Figures 5B, 5C:
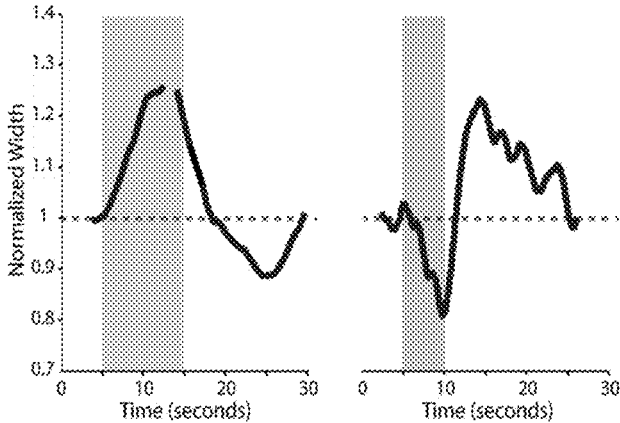
FIG. 5B is a graph showing the normalized width of an arteriole before, during, and after administration of amber light (560 nm). Endothelial cells of the arteriole were transduced to express Halorhodopsin 3.0. The X-axis shows the time and the Y-axis shows the normalized width of the arteriole.
FIG. 5C is a graph showing the normalized width of an arteriole before, during, and after administration of blue light (470 nm). Endothelial cells of the arteriole were transduced to express Channelrhodopsin-2. The X-axis shows the time and the Y-axis shows the normalized width of the arteriole.

Halorhodopsin-3.0 was selectively expressed in mouse ECs using transgenic mice bred to encode Cre-recombinase in ECs, and LoxP sequences flanking the fusion protein Halorhodopsin (eNpHR 3.0)-Enhanced Yellow Fluorescent Protein (Halo3.0-EYFP). An arteriole localized within the neocortex of a mouse (exemplary arteriole expressing Halo3.0-EYFP is shown in FIG. 5A). Amber light (560 nm) was administered as repeated brief pulses for the period indicated by the amber background in FIG. 5B to an arteriole in the neocortex of an awake mouse to elicit vascular dilation (FIG. 5B). As with many naturally-occurring events, these induced effects are sometimes followed (as shown here) by overshoot in the opposite direction.

Example 5: Control of Vascular Constriction with Endothelial Optogenetic Drive

The fusion protein Channelrhodopsin-2-Enhanced Yellow Fluorescent Protein (Ch2R-EYFP) was selectively expressed in mouse ECs using transgenic mice bred to encode Cre-recombinase in ECs, and LoxP sequences flanking the fusion protein Channelrhodopsin-2-Enhanced Yellow Fluorescent Protein (Ch2R-EYFP). An arteriole localized within the neocortex of a mouse (exemplary arteriole expressing Ch2R-EYFP is shown in FIG. 5A). Blue light (470 nm) was administered for the period indicated by the blue background in FIG. 5C to an arteriole in the neocortex of an awake mouse to elicit vascular constriction (FIG. 5C). As with many naturally-occurring events, these induced effects are sometimes followed (as shown here) by overshoot in the opposite direction.

Other Embodiments

While certain novel features of this invention shown and described are pointed out in the annexed claims, the invention is not intended to be limited to the details specified, since a person of ordinary skill in the relevant art will understand that various omissions, modifications, substitutions and changes in the forms and details of the invention illustrated and in its operation may be made without departing in any way from the spirit of the present invention. No feature of the invention is critical or essential unless it is expressly stated as being "critical" or "essential."

Those skilled in the art will recognize or be able to ascertain using no more than routine experimentation many equivalents to the specific embodiments of the invention described herein. Such equivalents are intended to be encompassed in the scope of the present invention.

All publications, patents, and patent applications mentioned in this specification are herein incorporated by reference to the same extent as if each independent publication, patent, or patent application was specifically and individually indicated to be incorporated by reference.

What is claimed is:

1. A method to deliver a therapeutic across the vascular endothelial barrier comprising endothelial cells expressing an optogenetic reagent in a subject, said method comprising the steps of: a) introducing said therapeutic into the blood stream of said subject; and b) contacting said endothelial cells with light, wherein said light activates said optogenetic reagent and thereby changes permeability of said endothelial cells and opens the vascular endothelial barrier such that said therapeutic in the blood stream crosses the vascular endothelial barrier.

2. The method of claim 1, wherein said optogenetic reagent is-selected from the group consisting of ChR1, ChR2, VChR1, ChR2 C128A, ChR2 C128S, ChR2 C128T, ChD, ChEF, ChF, ChIEF, NpHR, eNpHR, Arch 3.0, Arch T 3.0, Mac 3.0, melanopsin, and chimeras of these proteins.

3. The method of claim 1, wherein said optogenetic reagent are expressed in the endothelial cells by introducing a recombinant nucleic acid encoding the optogenetic reagent into said cells or precursors thereof.

4. The method of claim 3, wherein said recombinant nucleic acid is introduced into said cells by using any one or more of a virus, an electroporation device, a transfection method, and a transgenic method.

5. The method of claim 4, wherein said recombinant nucleic acid is encapsidated within a recombinant virus selected from the group consisting of recombinant adeno-associated virus (AAV), recombinant retrovirus, recombinant lentivirus, recombinant poxvirus, recombinant rabies virus, recombinant pseudo-rabies virus, recombinant herpes simplex virus, and human immunodeficiency virus (HIV).

6. The method of claim 5, wherein said recombinant nucleic acid encoding said optogenetic reagent further encodes a fiducial marker, that when expressed identifies cells infected by the recombinant virus.

7. The method of claim 6, wherein said fiducial marker is a fluorescent protein.

8. The method of claim 4, wherein said virus is applied using intravenous injection or applied locally to infect endothelial cells in specific regions.

9. The method of claim 1, wherein said light is applied using a laser or a light emitting diode, and wherein application of light is restricted to a defined spatial region of the body.

10. The method of claim 9, wherein said light is delivered using a fiber optic cable or catheter.

11. The method of claim 1, wherein said endothelial cells are part of a blood-air barrier in the lung.

12. The method of claim 11, wherein said method is used to treat a disease of the lung.

13. The method of claim 12, wherein said disease is a lung cancer.

14. The method of claim 1, wherein said therapeutic is selected from the group consisting of drugs, small molecules, peptides, proteins, antibodies, and nucleic acid molecules.

* * * * *